US00PP25244P3

(12) United States Plant Patent
Rankin

(10) Patent No.: US PP25,244 P3
(45) Date of Patent: Jan. 27, 2015

(54) ***ROSA* PLANT NAMED 'RANMD'**

(50) Latin Name: ***Rosa* hybrid**
Varietal Denomination: RANMD

(71) Applicant: Lloyd Rankin, Beaconsfield (AU)

(72) Inventor: Lloyd Rankin, Beaconsfield (AU)

( * ) Notice: Subject to any disclaimer, the term of this patent is extended or adjusted under 35 U.S.C. 154(b) by 138 days.

(21) Appl. No.: 13/815,777

(22) Filed: Mar. 14, 2013

(65) Prior Publication Data

US 2014/0283231 P1 Sep. 18, 2014

(51) Int. Cl.
*A01H 5/00* (2006.01)

(52) U.S. Cl.
USPC ..... Plt./134

(58) Field of Classification Search
USPC ..... Plt./134
See application file for complete search history.

*Primary Examiner* — Annette Para
(74) *Attorney, Agent, or Firm* — Cassandra Bright

(57) ABSTRACT

A new and distinct *Rosa* hybrid named 'RANMD' is disclosed, characterized by large, double, fragrant sulfur yellow flowers. Plants are vigorous and flowering continuously throughout the flowering season. Plant form is upright and bushy. The new cultivar is a *Rosa* typically suited for ornamental container and landscape use as well as cut flower production.

1 Drawing Sheet

Latin name of the genus and species: *Rosa* hybrid.
Variety denomination: 'RANMD'.

BACKGROUND OF THE INVENTION

The present invention relates to a new and distinct variety of *Rosa* hybrid, which has been named 'RANMD'. The novel variety described herein details a new and distinct variety of Rose plant of the Hybrid Tea class. The inventive variety was recognized to have merit for use as an ornamental shrub in landscape and container horticulture with the plant being grown in a range of container sizes suited to supply the retail nursery market and the commercial landscape market. The potential of the inventive variety as a cut flower for the floral industry was also recognized. Vase life trials were conducted to establish this suitability and it was found a vase life of 4 to 7 days may be expected, depending on treatment and environmental conditions.

The cultivar 'RANMD' was discovered as a naturally occurring branch mutation in 2002 in at a commercial nursery in Beaconfield, Victoria, Australia. This mutation was isolated by vegetative propagation and grown to a mature plant for further observation of its characters over the next 9 years. It has been found to reproduce from generation to generation with budding onto *Rosa multiflora* rootstock in a stable manner.

The new variety 'RANMD' was first asexually propagated by graft budding in the state of Victoria, Australia in 2002. The distinctive characteristics of cultivar 'RANMD' have remained stable and true to type through successive cycles of asexual propagation. Cutting propagation and tissue culture of the variety may also be used to reproduce the invention.

SUMMARY OF THE INVENTION

The cultivar 'RANMD' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RANMD'. These characteristics in combination distinguish 'RANMD' as a new and distinct *Rosa* hybrid cultivar:

1. Large, fragrant yellow flowers.
2. Vigorous growth.
3. Bushy plant habit.
4. Continuous production of flowers through the blooming season.
5. Suitability for potted, garden and cut flower production.

PARENTAL COMPARISON

The parent variety 'Valencia' is characterized by its apricot colored double flowers. The new variety, while similar in many horticultural characteristics to 'Valencia' produces flowers with a sulfur yellow coloration. Additionally plants of 'RANMD' are taller, bushier and more vigorous than plants of 'Valencia'.

COMMERCIAL COMPARISON

'RANMD' can also be compared to the Hybrid Tea Rose plant variety named 'Holtermann's Gold', unpatented. The plant growth habit of 'RANMD' is upright and bushy with a vigorous growth rate whereas the variety 'Holtermann's Gold' has a less bushy growth habit with lower vigor. The leaflets of 'RANMD' are broad whereas the leaflets of 'Holtermann's Gold' are narrow. The flowers of 'RANMD' are a light sulfur yellow color whereas 'Holtermann's Gold' has much deeper mustard yellow colored flowers. Additionally, flower of 'RANMD' have a strong fragrance whereas flowers of 'Holtermann's Gold' have a mild fragrance.

BRIEF DESCRIPTION OF THE PHOTOGRAPH

The accompanying photograph in FIG. 1 illustrates in full color typical flower development of 'RANMD'. The photograph was taken using conventional techniques and although colors may appear different from actual colors due to light reflectance it is as accurate as possible by conventional photographic techniques.

DETAILED BOTANICAL DESCRIPTION

The following is a detailed botanical description of a new and distinct variety of *Rosa* hybrid known as 'RANMD' based upon observations of 18-month old plants grown in 200 mm nursery pots in full sun in open beds in Beaconfield, Victoria, Australia during 2011 to 2013. Plant observations and descriptions were taken in late summer (February) 2013. Color references are made to The Royal Horticultural Society Colour Chart 2007, except where general terms of ordinary dictionary significance are used. No artificial light, photoperiodic treatments or chemical treatments were given to the plants. Measurements and numerical values represent averages of typical flowering types.

Botanical classification: *Rosa* hybrid 'RANMD'.

Age of the plant described: Approximately 1.5 years.

Container size of the plant described: 20 cm nursery pots.

PROPAGATION

Typical method: Vegetative cuttings.

Time to rooting: Approximately 20 days at 20° C.

Time to produce a rooted plantlet: Approximately 55 days at 15° C.

Root description: Fibrous.

PLANT

Growth habit: Upright and bushy.

Height: Approximately 125 cm.

Plant spread: Approximately 100 cm.

Rootstock: Budded onto *Rosa multiflora.*

Growth rate: Rapid.

Branching characteristics:

- *Length of primary branches.*—Approximately 60 to 80 cm.
- *Diameter of branches.*—Approximately 1 cm.
- *Quantity of branches.*—Average 10 to 12.
- *Branches-young wood.*—Diameter: Approximately 0.5 to 1.0 cm. Color: Near RHS Yellow-Green 146C. Texture: Smooth, with thorns. Thorns: Approximately density/quantity of thorns: Approximately 10 to 15 per 10 cm length of juvenile stem. Color: Near RHS Yellow-Green 146D. Length: Average 0.4 cm. Diameter: Average 0.5 cm.
- *Branches-old wood.*—Diameter: Approximately 1.5 cm. Texture: Smooth, with thorns. Thorns: Approximately density/quantity of thorns: Approximately 5 to 10 per 10 cm length of mature stem. Color: Near RHS Grayed-yellow 162B and 162C. Senescing to brown 200D with tip and base brown 200A. Length: Average 0.9 cm. Diameter: Average 1.0 cm. Shape: Concave profile with elliptic to obovate cross-sectional profile along basal abscission zone.

FOLIAGE

Leaf:

- *Arrangement.*—Alternate, pinnate.
- *Quantity.*—Approximately 20 per main branch, with 5 leaflets per leaf. Occasionally 3 leaflets per leaf.
- *Average length.*—Average 14 cm.
- *Average width.*—Average 10 cm.

Leaflets:

- *Terminal leaflet.*—Average Length: Average 5.5 to 6.0 cm. Average Width: Average 4.0 cm.
- *Lateral leaflet.*—Average Length: Average 5.0 cm. Average Width: Average 3.0 cm.
- *Shape of blade.*—Broad elliptic.
- *Apex.*—Acute.
- *Base.*—Obtuse.
- *Margin.*—Finely serrate.
- *Texture of top surface.*—Glabrous, leathery.
- *Texture of bottom surface.*—Glabrous, leathery.
- *Appearance of top surface.*—Semi-glossy.
- *Appearance of top surface.*—Matte.
- *Leaf internode length.*—Average 2.0 to 5.0 cm.
- *Color.*—Young foliage upper side: Near RHS Green 137B. Young foliage under side: Near RHS Yellow-Green 147C. Mature foliage upper side: Near RHS Green N137B. Mature foliage under side: Near RHS Yellow-Green 148C.
- *Venation.*—Type: Reticulate. Venation color upper side: Near RHS Green N137B. Venation color under side: Near RHS Yellow-Green 148C, mid rib Yellow-Green 152B and 152C, both colors present.
- *Leaflet petiole.*—Length: 0.25 cm. Width: 0.2 cm. Color: Near RHS Yellow-Green 146D. Juvenile foliage leaflet petioles tinged with Greyed-Red 178A or Greyed-Orange 174A. Texture: Glabrous.
- *Rachis.*—Length: 2 cm. Width: 0.2 cm. Color: Near RHS Yellow-Green 146D. Texture: Glabrous.
- *Stipules.*—Average Length: Average 1.8 to 2.2 cm. Average Width: Average 0.4 to 0.5 cm. Shape: Longitudinally flanged. Apex: Acute. Base: Clasping. Margin: Entire with stipitate glands. Texture of top surface: Tomentose. Texture of bottom surface: Tomentose. Color: Near Yellow-Green 146 D, all surfaces.

FLOWER

Natural flowering season: Continuous flowering from late Spring to mid Fall.

Begins flowering after how many years/months: Approximately 4 months from a graft budded plant.

Inflorescence type and habit: Singly occurring full, double flowers, with a flattened upper profile.

Flower longevity on plant: Average 12 to 14 days.

Vase life: 5 to 7 days.

Fragrance: Strong, citrus and fruit scented, along with soft typical tea rose scent.

Quantity of flowers: Normally 1 per stem, with very few flowering laterals.

Inflorescence size:

- *Diameter.*—Average 11 to 15 cm. Largest flowers up to 18 cm.
- *Depth.*—Approximately 7 to 10 cm.

Peduncle:

*Length*.—Approximately 8.0 to 9.0 cm.

*Diameter*.—Approximately 0.4 mm.

*Texture*.—Smooth.

*Color*.—Near RHS yellow-Green 146D.

Petals:

*Petal arrangement*.—Imbricate whorls.

*Quantity of petals*.—60 to 65.

*Size*.—Length: Approximately 5.0 to 5.5 cm. Width: Approximately 4.0 to 4.5 cm.

*Shape*.—Obovate.

*Margin*.—Entire.

*Apex*.—Rounded.

*Base*.—Obtuse.

*Texture*.—Smooth, leathery all surfaces.

*Color*.—Petals: When opening: Upper surface: Near RHS Yellow 12B. Lower surface: Near RHS Yellow 12B. Fully opened: Upper surface: Near RHS Yellow 12B. Lower surface: Near RHS Yellow 12B. Color Changes when aging: Near RHS Yellow 10B, all surfaces.

Bud:

*Shape*.—Ovate.

*Length*.—Approximately 4.0 cm.

*Diameter*.—Approximately 1.5 to 1.8 cm.

*Color*.—Near RHS Greyed-Red 178A as calyx breaks open.

Sepals:

*Quantity*.—5.

*Length*.—Approximately 4.0 to 4.0 cm.

*Width*.—Approximately 1.1 to 1.2 at base cm.

*Shape*.—Deltate.

*Aspect*.—Reflexed down with flower maturity.

*Color*.—Upper Surface: Near RHS Yellow-Green 146B, center Yellow-Green 148C. Lower Surface: Near RHS Yellow-Green 147B.

*Texture*.—Upper Surface: Tomentose. Lower Surface: Smooth.

Petaloids: Not present.

REPRODUCTIVE ORGANS

Stamens:

*Number*.—Approximately 130 to 150.

*Filament length*.—Approximately 0.5 cm.

*Filament color*.—Near RHS Yellow-Orange 23D.

Anthers:

*Length*.—2.5 mm.

*Shape*.—Narrow ovate.

*Color*.—Near RHS Yellow-Orange 23A.

*Pollen*.—Not observed.

Pistil:

*Number*.—Approximately 95.

*Length*.—Approximately 2.2 mm.

*Color*.—Near RHS Greyed-Yellow 160C.

*Style*.—Length: Approximately 0.7 mm. Color: Near RHS White 155D.

*Stigma*.—Length: Approximately 1.5 mm. Color: Near RHS Yellow 12C.

OTHER CHARACTERISTICS

Hips:

*Length*.—12 to 18 mm.

*Width*.—12 to 14 mm.

*Shape*.—Funnel shaped.

*Color*.—Near RHS Yellow-Green 146B. Not observed to change color.

*Seeds*.—Seed production not observed.

Disease/pest resistance: Average resistance to Powdery mildew (*Sphaerotheca pannosa* and blackspot (*Diplocarpon rosae*) under normal growing conditions. Can be affected by Downy Mildew (*Peronospora sparsa*) in conducive conditions.

Temperature tolerance: Typical tea rose temperature tolerance.

What is claimed is:

1. A new and distinct cultivar of *Rosa* hybrid plant named 'RANMD' as herein illustrated and described.

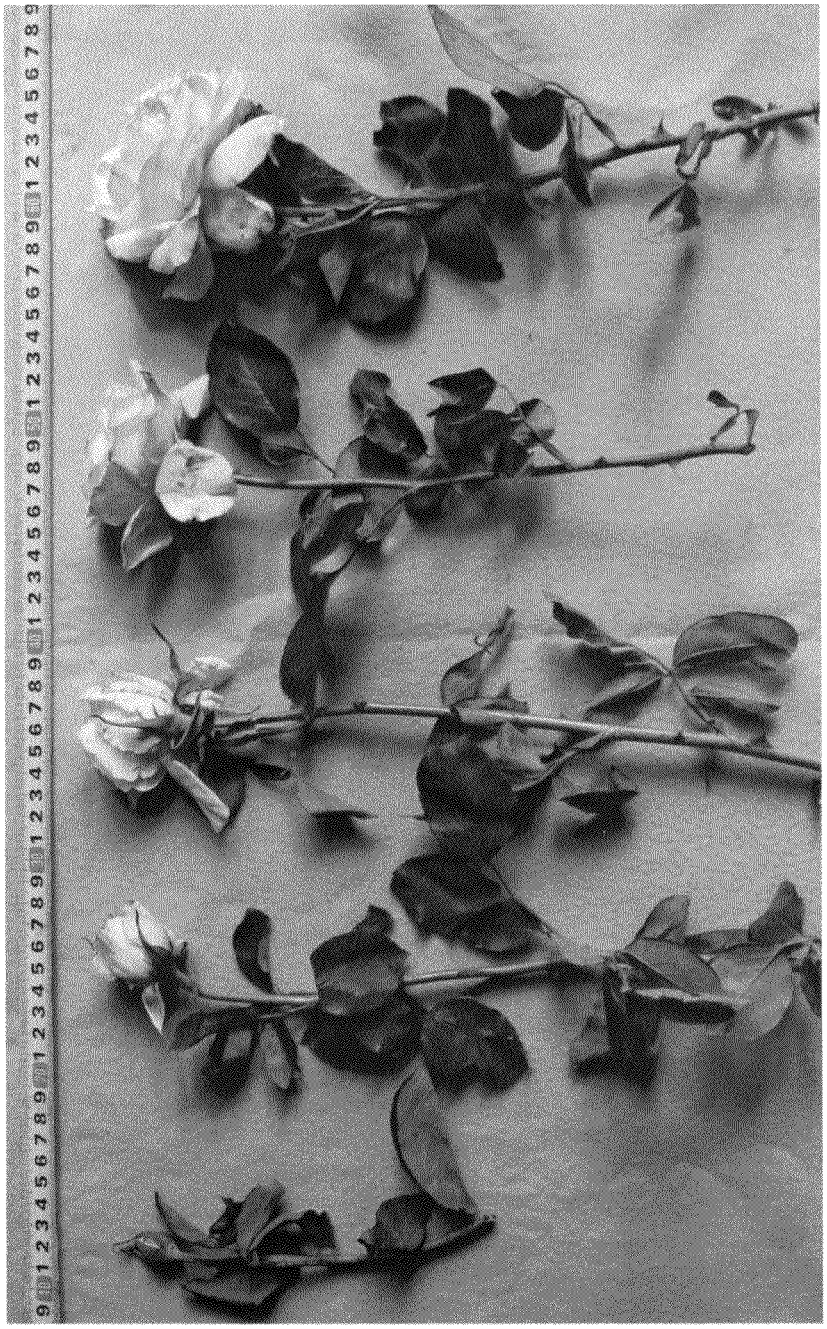

* * * * *